United States Patent
De Ceuster et al.

(10) Patent No.: US 11,636,923 B2
(45) Date of Patent: Apr. 25, 2023

(54) METHODS AND SYSTEMS FOR OPERATING A HIGH PRESSURE ETHYLENE POLYMERIZATION UNIT

(71) Applicant: ExxonMobil Chemical Patents Inc., Baytown, TX (US)

(72) Inventors: Steven R. De Ceuster, Zoersel (BE); Ludo W. J. Alen, Westerlo (BE); Daniel E. Milam, Hellevoetsluis (NL)

(73) Assignee: ExxonMobil Chemical Patents Inc., Baytown, TX (US)

( * ) Notice: Subject to any disclaimer, the term of this patent is extended or adjusted under 35 U.S.C. 154(b) by 1060 days.

(21) Appl. No.: 16/311,214

(22) PCT Filed: Apr. 20, 2017

(86) PCT No.: PCT/US2017/028601
§ 371 (c)(1),
(2) Date: Dec. 19, 2018

(87) PCT Pub. No.: WO2018/004792
PCT Pub. Date: Jan. 4, 2018

(65) Prior Publication Data
US 2019/0244682 A1 Aug. 8, 2019

Related U.S. Application Data

(60) Provisional application No. 62/356,846, filed on Jun. 30, 2016.

(51) Int. Cl.
*G16C 20/10* (2019.01)
*C08F 2/01* (2006.01)
(Continued)

(52) U.S. Cl.
CPC ............... *G16C 20/10* (2019.02); *C08F 2/01* (2013.01); *C08F 110/02* (2013.01);
(Continued)

(58) Field of Classification Search
CPC ....... G05B 15/00; G05B 19/418; C08F 10/02; C08F 110/02; C08F 210/02; C08F 210/16; C08F 218/08; C08F 2/01; C08F 2400/04
(Continued)

(56) References Cited

U.S. PATENT DOCUMENTS 4,668,473 A 5/1987 Agarwal
6,936,665 B2 * 8/2005 Stephens ................... B01J 8/10
526/67

(Continued)

OTHER PUBLICATIONS

Asteasuain, M.; Bradnolin, A. Computers and Chemical Engineering 2008, 32, 396-408. (Year: 2008).*

(Continued)

*Primary Examiner* — Rip A Lee
(74) *Attorney, Agent, or Firm* — ExxonMobil Chemical Patents Inc.-Law Department

(57) ABSTRACT

Disclosed are high-pressure polymerization methods and systems using optimized operation sequence logic established at least partly from an analysis of a database containing data of previous operations. The optimized operation sequence logic and collected current process and system data are used to automate the operation of a high pressure ethylene polymerization process and unit.

24 Claims, 2 Drawing Sheets

(51) Int. Cl.
*C08F 110/02* (2006.01)
*C08F 210/02* (2006.01)
*C08F 218/08* (2006.01)
*G05B 15/00* (2006.01)
*G05B 19/418* (2006.01)

(52) U.S. Cl.
CPC .......... *C08F 210/02* (2013.01); *C08F 218/08* (2013.01); *C08F 2400/04* (2021.01); *C08F 2500/01* (2013.01); *G05B 15/00* (2013.01); *G05B 19/418* (2013.01)

(58) Field of Classification Search
USPC ............................. 526/59, 64, 330, 331, 352
See application file for complete search history.

(56) References Cited

U.S. PATENT DOCUMENTS

| | | | |
|---|---|---|---|
| 8,187,546 | B2 | 5/2012 | Barbero |
| 2003/0073787 | A1 | 4/2003 | Stephens et al. |
| 2007/0250214 | A1 | 10/2007 | Lee et al. |
| 2010/0004407 | A1 | 1/2010 | Goossens et al. |
| 2011/0276164 | A1 | 11/2011 | Bourg, Jr. et al. |
| 2014/0171601 | A1 | 6/2014 | Bhandarkar et al. |

OTHER PUBLICATIONS

Asteasuain, M. et al., "Modeling and Optimization of a High-Pressure Ethylene Polymerization Reactor Using gPROMS", Computers & Chemical Engineering, vol. 32, Issue 3, pp. 396-408, (2008).

Asteasuain M., et al. "Dynamic Simulation and Optimisation of Tubular Polymerisation Reactors in gPROMS", Computers & Chemical Engineering, vol. 25, Issues 4-6, pp. 509-515 (2001).

Kiparissides C. et al., "On-Line Optimization of a High-Pressure Low-Density Polyethylene Tubular Reactor", Chemical Engineering Science, vol. 49, Issue 24, Part 2, pp. 2011-5024 (1994).

Montague, J., "ExxonMobil Automates Procedures, Reaps Benefits", Control, Articles, 2015, pp. 1-2 , http://www.controlglobal.com/articles/2015/hug-8/.

Sandip Kumar Lahiri et al., (2009) "Process Modeling and Optimization of Industrial Ethylene Oxide Reactor by Integrating Support Vector Regression and Genetic Algorithm" The Canadian Journal of Chemical Engineering vol. 87, Feb. 2009, pp. 118-128.

Wang Tianpu, (2004), "Study on Optimization Strategy of Polyolefin Production Process", Chinese Doctoral Dissertations & Master's Theses, full text database (Doctor) Engineering Science and Technology I, No. 3, pp. B016-17, published in China Sep. 15, 2004. (attached hereto is the English translation of Chinese Office Action, as explanation of relevance).

\* cited by examiner

METHODS AND SYSTEMS FOR OPERATING A HIGH PRESSURE ETHYLENE POLYMERIZATION UNIT

CROSS-REFERENCE OF RELATED APPLICATIONS

This application is a National Phase Application claiming priority to PCT Application Serial No. PCT/US2017/028601 filed Apr. 20, 2017, which claims priority to U.S. Provisional Application No. 62/356,846 filed Jun. 30, 2016, hereby incorporated by reference in their entireties.

FIELD OF THE INVENTION

The invention relates to a method and a system for operating a high pressure ethylene polymerization unit. In particular, the invention relates to a method and a system using optimized operation sequence logic that automates operation of a high pressure ethylene polymerization unit.

BACKGROUND OF THE INVENTION

High pressure reactors, such as tubular reactors and autoclaves, are used for the polymerization of ethylene at high pressure, for example, pressures of over 1000 bar (100 MPa), and up to 3000 bar (300 MPa) or higher. In such processes, fresh ethylene from an ethylene supply is compressed sequentially by a primary compressor and a second compressor to reactor pressure and then combined, in the reactor, with initiators and any comonomers, if available, and is polymerized to give a mixture comprising principally polymer and unreacted monomer. That mixture leaves the reactor through a valve, generally referred to as a high pressure let down valve, and then enters a separation system in which unreacted monomer is separated from the polymer and recycled back to the suction of the secondary compressor where it is combined with the fresh ethylene from the primary compressor.

It was announced on Jun. 23, 2015, that ExxonMobil launched use of Honeywell's Procedural Operations solution to improve margins, reduce workloads at its refineries and chemical plants (http://www.controlglobal.comL/articles/2015/hug-8/).

Currently, operation procedures of the high pressure polymerization process and reactor is conducted by operators, which suffers from disadvantages caused by instability in manual operation, including loss of operator experience due to staff turnover, off-quality products due to failure of compliance with standard procedures, and suboptimal reactor control due to misuse of historical data instead of up-to-date data. Therefore, there remains a need in the art for a solution that can provide improved control over the ethylene polymerization unit with reduced occurrence of operation upsets. Applicant has found that such purpose can be achieved by replacing complex operation procedures traditionally done by operators with optimized operation sequence logic, which may comprise a number of Distributed Control System (DCS) programs jointly mimicking operation knowledge of operators and engineers. Particularly, knowledge of experienced operators, including troubleshooting in case of abnormal situations, is captured in programs and an operator interface so that operation procedures can be automated and, in turn, actions in response to real-time reactor conditions can be automatically performed. Such optimized operation sequence logic can deliver desired continuity and stability in human expertise while diminishing likelihood of human error during operation, leading to efficient and steady running of an ethylene polymerization unit with reduced disruption from sudden upsets.

SUMMARY OF THE INVENTION

Provided are methods and systems for operating a high pressure ethylene polymerization unit.

The method comprises: (I) collecting data from previous operations; (II) building a database including the collected data of previous operations; (III) analyzing the database; (IV) establishing an optimized operation sequence logic; (V) collecting current data of a current operation; and (VI) conducting the current operation according to the optimized operation sequence logic and current data.

The method may include one of more of the following processes implementing at least steps (IV), (V), and (VI): starting up a reactor in the ethylene polymerization unit; switching the operation from conditions optimized for producing a first product to conditions optimized for producing a second product; defouling the reactor, defouling a recycle; and packing a modifier for the reactor.

The high pressure ethylene polymerization unit system comprises: a computer system, a reactor, multiple sensors, and multiple actuators, wherein the computer system stores an optimized operation sequence logic, receives operation data from the multiple sensors, and controls the reactor and the actuators according to the optimized operation sequence logic and the operation data.

DETAILED DESCRIPTION

Figure 1:
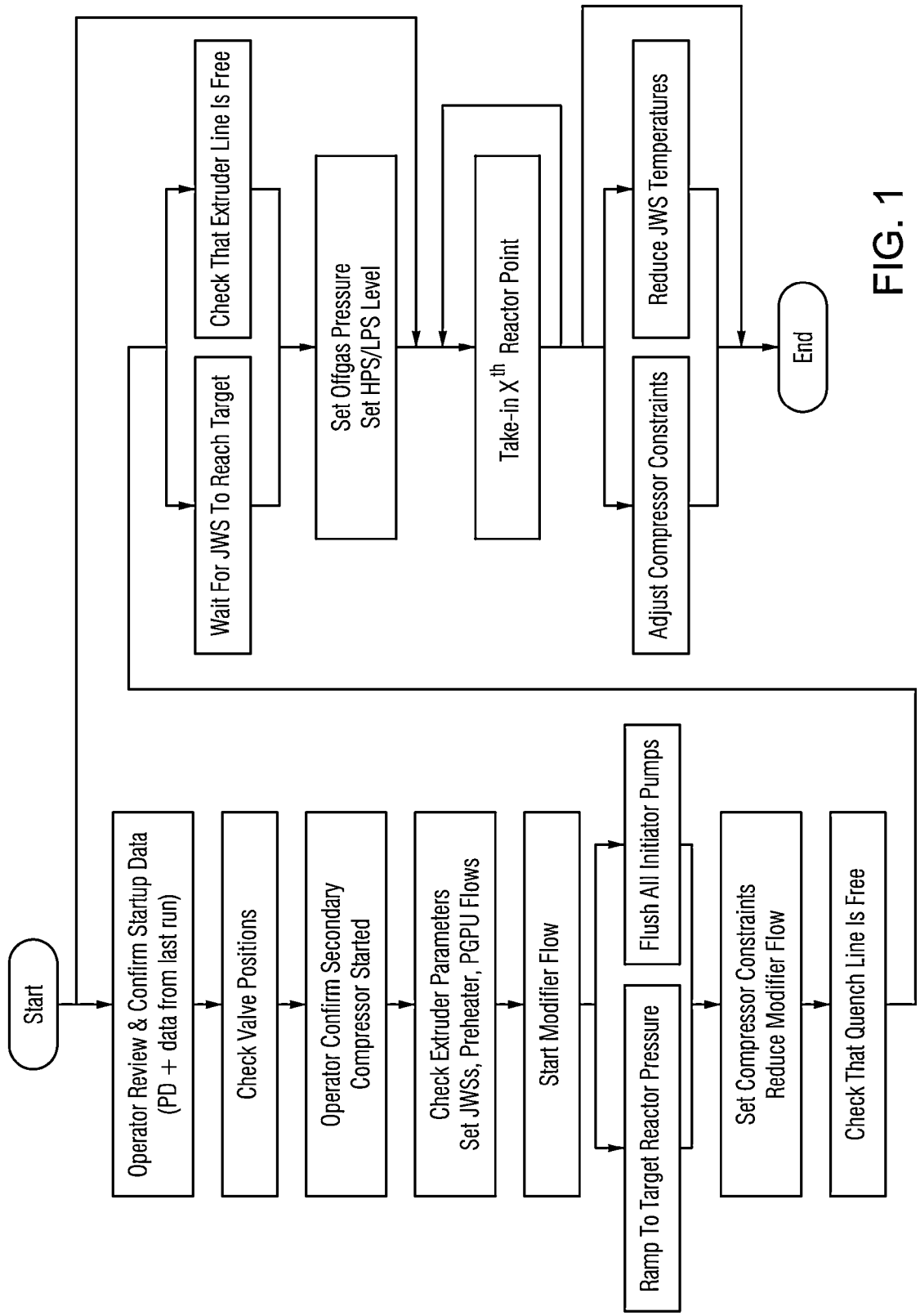
FIG. 1 depicts a summary flowchart showing an optimized operation sequence logic for a reactor start-up process according to one embodiment of the present invention.

Various specific embodiments, versions of the present invention will now be described, including preferred embodiments and definitions that are adopted herein. While the following detailed description gives specific preferred embodiments, those skilled in the art will appreciate that these embodiments are exemplary only, and that the present invention can be practiced in other ways. Any reference to the "invention" may refer to one or more, but not necessarily all, of the present inventions defined by the claims. The use of headings is for purposes of convenience only and does not limit the scope of the present invention.

As used herein, "high pressure polymerization" refers to a highly exothermic polymerization reaction that is performed in reactors, such as tubular reactors and autoclaves, under high reactor operating pressures, for example, of over 1000 bar (100 MPa), and up to 3000 bar (300 MPa) or higher.

As used herein, Distributed Control System (DCS) refers to a control system for a process or plant, wherein control elements are distributed throughout the system. A DCS typically uses custom designed processors as controllers and uses both proprietary interconnections and standard communications protocol for communication. Input and output modules form component parts of the DCS. The processor receives information from input modules and sends information to output modules. The input modules receive information from input instruments in the process (or field) and the output modules transmit instructions to the output instruments in the field. The inputs and outputs can be either analog signal which are continuously changing or discrete signals which are two state either on or off. Computer buses or electrical buses connect the processor and modules through multiplexer or demultiplexers. Buses also connect the distributed controllers with the central controller and finally to the Human-machine interface (HMI) or control consoles. DCSs are used to control manufacturing processes that are continuous or batch-oriented. DCSs are connected to sensors and actuators and use setpoint control to control the flow of material through the plant. The most common example is a setpoint control loop consisting of a pressure sensor, controller, and control valve. Pressure or flow measurements are transmitted to the controller, usually through the aid of a signal conditioning input/output (I/O) device. When the measured variable reaches a certain point, the controller instructs a valve or actuation device to open or close until the fluidic flow process reaches the desired setpoint. A typical DCS consists of functionally and/or geographically distributed digital controllers capable of executing from 1 to 256 or more regulatory control loops in one control box. The input/output devices (I/O) can be integral with the controller or located remotely via a field network. Today's controllers have extensive computational capabilities and, in addition to proportional, integral, and derivative (PID) control, can generally perform logic and sequential control. DCSs are usually designed with redundant processors to enhance the reliability of the control system. Most systems come with displays and configuration software that enable the end-user to configure the control system without the need for performing low-level programming, allowing the user also to better focus on the application rather than the equipment. However, considerable system knowledge and skill is required to properly deploy the hardware, software, and applications. Many plants have dedicated personnel who focus on these tasks, augmented by vendor support that may include maintenance support contracts. DCSs may employ one or more workstations and can be configured at the workstation or by an off-line personal computer. Local communication is handled by a control network with transmission over twisted-pair, coaxial, or fiber-optic cable. A server and/or applications processor may be included in the system for extra computational, data collection, and reporting capability.

As used herein, Procedural Operations (ProcOps) refers to an application developed by Honeywell International, helping users automate and manage operating procedures. It provides intuitive, step-by-step information and feedback on execution status, transition conditions and related process variables so that the procedure is completed efficiently, freeing the operator for other tasks. With ProcOps, users can automate procedures depending on their existing and desired level of automation. In addition, Procedural Operations allows automated control of offline manual procedures within Experion®. The control system can interact with operators for manual procedures, providing instructions and warnings as given in the written procedures for safe and reliable operations. It uses pre-built tabular and flowchart displays to show all procedural actions in a function-filled format to operators. Further, it provides operator-centric procedure execution status with the right information presented to the operator in the context of the active task. Part of the Experion PKS system, it provides a single, consistent environment for all operations whether it is operator actions, automatic monitoring, automated control or alarming.

In the process of the present invention, data of previous operations are collected. Such data can be based on experience of operators, sensor readouts, equipment specifications, process specifications, raw material property data, product property data, safety thresholds data, audio or video recordings of operation instructions and actual operations, and the like.

A database including the collected data of previous operations is then built. Experienced engineers and operators may be able to build the database in their minds, on paper, or in other physical media as traditionally used. Preferably, the database is stored in electronic media such as computers. The ability to capture and store vast amount of data, in highly logical and organized order by modern computers makes it possible to record useful data from virtually all previous operations. Advantageously, the data in the database are categorized, indexed, and easily retrievable.

The database is then analyzed to decide one or more the steps to be taken in current and future operations, conditions under which the steps are triggered, conditions under which the steps are taken, duration of the step, and orders of the steps. The analysis can be partly done by human mind, such as the judgment of an experienced operator or engineer. Alternatively, the analysis can be conducted by a computer system, based on pre-determined algorithm, or using artificial intelligence. The analysis can be based on a small set of data, or a large set of data. In the latter case, sophisticated computers with deep learning capability can be advantageously used for mining process improvement opportunities.

The optimized operation sequence logic is a set of possible operation steps connected via a logical relation tree. The operation steps can be included into the sequence logic by design based on scientific and engineering principles, knowledge gained and collected from previous experiences of operators and engineers, equipment and process manuals from the manufacturer accompanying the various equipment, or legal requirements such as laws and regulations. The onset of each specific step, its duration, the conditions under which it runs, its termination, and the like, can be determined by one or more process variables. The order of multiple steps is also determined by multiple variables, which can fluctuate over time, and from operation to operation. The variables may change over time as equipment age, feed material change, natural environment change, etc. Therefore, it is highly desired that the optimized operation sequence logic is optimized before each operation, so that as many as possible previous lessons learned are taken into consideration. The optimization can take one of more of the following forms, among others: (i) adding or deleting a new branch on the logic relation tree; (ii) adding or deleting a parameter that triggers the onset or termination of a step; (iii) changing the threshold value of a parameter that determines the duration of a step; (iv) changing the function used for calculating the duration of a step; and (v) changing a process condition, such as temperature, pressure, flow rate, and the like, directly. The optimization can be for one or more purposes that may differ from time to time, such as: (a) maximizing output; (b) ensuring quality of product; (c) ensuring safety; (d) energy conservation; (e) cost reduction; and the like.

Any current operation of the system includes collection of current operation data from, e.g., sensors, raw material suppliers, equipment suppliers, utility suppliers, calculation or logic deduction form prior operations, observation of operators on site, and the like. Desirably, current operation data are automatically generated by sensors and then sent to the computer system for processing.

The current operation is then carried out following the optimized operation sequence logic based on the current operation data collected. The current data may be used for determining the actual operation step sequence, the onset and termination of a specific step, the duration of each step, the conditions under which the step is run, according to the optimized operation sequence logic. It is desirable that the system is being monitored in real time, any input data is sent to the computer system immediately, the right steps and their sequence are calculated immediately, and instructions are sent to the actuators, other equipment, and controls at the right time and as soon as possible, with minimal time lag. Reliable and smooth running of a large, complex reaction system including many components under various conditions can benefit enormously from the automated "intelligent" process of the present invention.

One advantage of the present invention process is its capability to memorialize positive and negative previous lessons learned about the process and equipment, to allow for optimizing the process and equipment based on the lessons learned, to take into considerations of many different variables with different level of priority simultaneously, to make the optimized decision on process and equipment change with the highest speed, and to achieve flexible production of multiple products from the same system with high quality and short turn-around time.

In a class of embodiments, a method for operating a high pressure ethylene polymerization unit may comprise operating reactor start-up, grade transition, reactor defouling, recycle defouling, and modifier packing for start-up, wherein at least one of reactor start-up, grade transition, recycle defouling, and modifier packing for start-up is operated by optimized operation sequence logic.

Reactor Start-Up

In one preferred embodiment where the process of the present invention is used for operation of reactor start-up, the optimized operation sequence logic may vary with specific procedures of different plants but typically automates operation procedures from starting secondary compressor to putting the reactor in normal conditions.

Once the operator starts up a reactor line, data is automatically collected about the last shutdown and the operator enters data about what mechanical work took place during the shutdown. In one preferred embodiment, the optimized operation sequence logic in the reactor start-up may differentiate between the following starting conditions to start the program path from different starting points accordingly: (a) whether the reactor comes out of a short or prolonged shutdown; (b) whether the shutdown occurred while a vinyl acetate (VA) grade is being produced; (c) whether an oxygen analyzer check is needed; (d) whether a reactor pressure test is needed; (d) whether compressor cylinders are changed during the shutdown; (e) whether the shutdown is an emergency shutdown or a controlled shutdown.

In another embodiment, with reference to FIG. 1, the optimized operation sequence logic in the reactor start-up comprises the step of taking reactor points in service, which step is not completed until all the reactor points (X is the number of reactor points) are brought in service. In one preferred embodiment, before the step of taking reactor points in service, the optimized operation sequence logic further comprises the steps of: (a) operator reviewing and confirming startup data (based on Process Directives (PD) and/or data from last running cycle); (b) checking valve positions; (c) starting secondary compressor; (d) operator confirming secondary compressor started; (e) checking extruder parameters and setting JWS, preheaters, and purge gas purification unit (PGPU) flows; (f) starting modifier flow; (g) ramping to target reactor pressure and flushing all initiator pumps; (h) setting compressor constraints and reducing modifier flow; (i) checking that quench line is free; (j) waiting for JWS to reach target and checking that extruder line is free; (k) setting offgas pressure, high pressure separation (HPS) level, and low pressure separation (LPS) level. In another preferred embodiment, after the step of taking reactor points in service, the optimized operation sequence logic further comprises the step of adjusting compressor constraints and reducing JWS temperature. The optimized operation sequence logic may start directly with the step of taking reactor points in service when items in steps (a) to (k) are already in place after the last running cycle.

During execution, the optimized operation sequence logic in the reactor start-up may keep monitoring abnormal conditions and, if any is detected, may immediately take appropriate action for troubleshooting while pausing normal operation. Examples of the abnormal conditions include without limitation the following: (a) point loss; (b) oxygen detected; (c) low steam pressure; (d) modifier flow deviation from desired flow; (e) back pressure alarm while a reactor point is being taken in service; and (f) activation of interlocks.

In yet another embodiment, the optimized operation sequence logic in the reactor start-up uses a Procedural Operations sequence for automation of start-up operation to manipulate more than 20 controllers based on hundreds of inputs. The program run time may be about four to five hours.

The optimized operation sequence logic in the reactor start-up is capable of taking tens of actions simultaneously and assessing a multitude of conditions continuously, greatly increasing the operation efficiency achievable with even an experienced operator. Use of such program in the reactor start-up can save lost opportunities during the reactor start-up operation, and as a result, issues including production loss, off-test product, and equipment reliability can be well addressed.

Grade Transition

In one embodiment where optimized operation sequence logic is used for operation of grade transition, the optimized operation sequence logic automates operation procedures from the beginning of the last batch in the old grade to the end of the first batch in the new grade.

In one preferred embodiment, the optimized operation sequence logic in the grade transition may comprise changing initiator, reactor pressure, reactor temperature, modifier flow, and JWS temperature control.

The optimized operation sequence logic is not limited by any particular grade transition and may be used for any known grade transition. Preferably, the grade transition described herein is at least one of transition from and to VA grades, transition from and to medium density grades, switching initiator codes, switching modifier between propylene, propionaldehyde (PA), and a mixture of propylene and PA.

During execution, the optimized operation sequence logic in the grade transition may keep monitoring abnormal conditions and, if any is detected, may immediately take appropriate action for troubleshooting while pausing normal operation. Examples of the abnormal conditions include without limitation the following: (a) point loss; (b) back pressure alarm; (c) rod loading constraints on high pressure compressor; and (d) modifier flow deviation from desired flow.

In another preferred embodiment, the optimized operation sequence logic in the grade transition uses a Procedural Operations sequence for automation of grade transition operation.

Use of such program in the grade transition can save lost opportunities during the grade transition operation, and as a result, issues including production loss, off-test product, and equipment reliability can be well addressed.

Reactor Defouling

Figure 2:
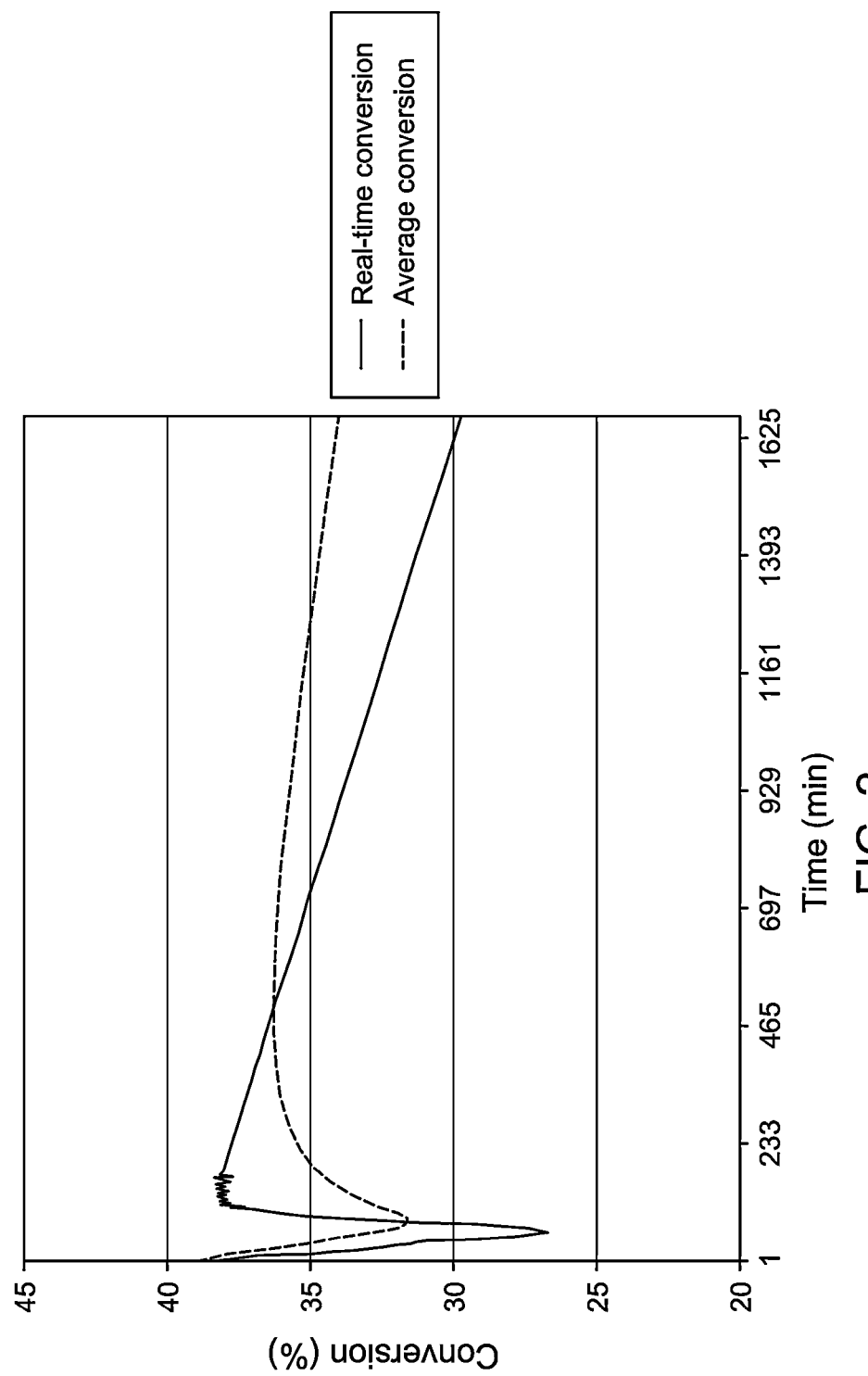
FIG. 2 depicts the timing of starting a new defouling cycle as determined by evolution of real-time conversion over time in comparison with average conversion.

The starting point of reactor defouling is suggested by evolution of the conversion over time as demonstrated in FIG. 2. The average conversion/production over the entire cycle of defouling-fouling shall be calculated and continuously compared to the real-time conversion/production. Specifically, a new defouling cycle is started upon the moment when average conversion from the beginning of the previous defouling cycle exceeds real-time conversion since the average conversion keeps decreasing from the point on.

In one preferred embodiment, the defouling may comprise the steps of: (i) from the JWS at the beginning of the reactor to that at the end of the reactor, increasing JWS temperatures by heating the water in the JWS to a defouling target temperature, preferably in the range of about 180° C. to about 200° C.; (ii) keeping all temperatures at their respective defouling target for a period of time as determined by calculating defouling degree based on a correlation of JWS temperatures with light-off temperatures; and (iii) decreasing the temperatures to a recipe value, e.g., below 90° C., also from the beginning to the end of the reactor.

Typically, the correlation of the JWS temperatures with light-off temperatures, which can be a reference reactor inlet temperature typically from the first inlet zone without a side stream, is almost linear until the defouling starts. From that point on, the linear correlation is lost due to changes in the heat transfer coefficient resulted from the defouling, which alters the physical environment. Once deviation from the linear correlation stops increasing, no further physical change is observed, indicating that no further defouling is going on, upon which moment defouling is stopped to prevent capacity loss.

During the defouling, less polyethylene is produced and, thus, the modifier flow needs to be changed. Accordingly, the modifier concentration setpoint is adjusted at multiple, e.g., as many as thirty, time points throughout the defouling process. The changes are dependent on the particular running grade and are determined by heuristic data.

Automation of the reactor defouling operation allows defouling in each of the reactors proceed consistently to avoid capacity loss and off-production to the maximum extent by virtue of programmed expertise.

Recycle Defouling

In one preferred embodiment where optimized operation sequence logic is used for operation of recycle defouling, the optimized operation sequence logic automates increasing and decreasing temperatures of hot, intermediate and low coolers for each train, and changing modifier control and reactor peak temperature while taking into account the rod load constraints.

Use of such program in the recycle defouling can save lost opportunities during the recycle defouling operation, and as a result, issues including production loss, off-test product, and equipment reliability can be well addressed.

Modifier Packing for Start-Up

In one preferred embodiment where optimized operation sequence logic is used for operation of modifier packing for start-up, the optimized operation sequence logic automates injecting an amount of modifier after a start-up. The amount of modifier is determined by required concentration of the modifier for a particular grade and total amount of the modifier and VA remaining in the unit, wherein the former is within knowledge and experience of operator while the latter requires more complex analysis as follows. To determine the modifier and VA remaining in the unit, the reactor line is split up into several segments, i.e., reactor, high pressure recycle, secondary compressor, high pressure separator, etc. The lowest pressure since the shutdown is recorded for each segment for determining the lowest contents in the segment before it is refilled with pure ethylene. For each segment the remaining modifier and VA are calculated based on the lowest content and the concentrations at shutdown. The remaining modifier and VA in the entire system can be determined by the sum of the remaining modifiers in all segments, which, in combination with required concentration of the modifier for a particular grade, can decide on a proper amount of modifier for injection immediately after a start-up to avoid mechanical problems and bad quality.

Also provided are systems for operating a high pressure ethylene polymerization unit. A system for operating a high pressure ethylene polymerization unit may comprise optimized operation sequence logic as described herein in at least one of reactor start-up, grade transition, reactor defouling, recycle defouling, and modifier packing for start-up.

In one embodiment, a high pressure ethylene polymerization unit may be operated by optimized operation sequence logic described herein in at least one of reactor start-up, grade transition, reactor defouling, recycle defouling, and modifier packing for start-up during polymerization reaction.

All documents described herein are incorporated by reference herein in their entirety unless otherwise stated. When numerical lower limits and numerical upper limits are listed herein, ranges from any lower limit to any upper limit are contemplated. As is apparent from the foregoing general description and the specific embodiments, while forms of the invention have been illustrated and described, various modifications can be made without departing from the spirit and scope of the invention. Accordingly, it is not intended that the invention be limited thereby.

What is claimed is:

1. A method for operating a high pressure ethylene polymerization unit, comprising:
   (I) collecting data from previous operations;
   (II) building a database including the collected data of previous operations;
   (III) analyzing the database;
   (IV) establishing computer coding embodying an optimized operation sequence logic;
   (V) collecting real-time data of a current operation; and
   (VI) conducting one or more next steps of the current operation according to the optimized operation sequence logic and current data at least partly by using an automated computer system.

2. The method of claim 1, which includes a process of starting up a reactor in the ethylene polymerization unit comprising at least steps (IV), (V), and (VI).

3. The method of claim 2, wherein the optimized operation sequence logic in step (IV) considers at least the following process variables:
   (a) whether the reactor comes out of a short or prolonged shutdown length of time of a reactor shutdown;
   (b) whether a shutdown occurred while a vinyl acetate (VA) grade of polyethylene was being produced;

(c) whether an oxygen analyzer check is needed;
(d) whether a reactor pressure test is needed;
(e) whether compressor cylinders are changed during a shutdown; and
(f) whether a shutdown was an emergency shutdown or a controlled shutdown.

4. The method of claim 2, wherein the optimized operation sequence logic in step (IV) of the process of starting up the reactor comprises a step of taking reactor points in service.

5. The method of claim 4, wherein the optimized operation sequence logic further comprises before implementing the step of taking reactor points in service deciding on whether to carry out one or more of the following steps and their sequences:
(a) reviewing and confirming startup data by operator;
(b) checking valve positions;
(c) starting secondary compressor;
(d) operator confirming secondary compressor started;
(e) checking extruder parameters and setting jacket water systems (JWSs), preheaters, and purge gas purification unit (PGPU) flows;
(f) starting modifier flow;
(g) ramping to target reactor pressure and flushing all initiator pumps;
(h) setting compressor constraints and reducing modifier flow; checking that quench line is free; waiting for JWS to reach target and checking that extruder line is free; and
(k) setting offgas pressure, high pressure separation (HPS) level, and low pressure separation (LPS) level.

6. The method of claim 4, wherein the optimized operation sequence logic further comprises after the step of taking reactor points in service a step of adjusting compressor constraints and reducing JWS temperature.

7. The method of claim 2, wherein the optimized operation sequence logic in the reactor start-up uses a means for a procedural operations sequence.

8. The method of claim 2, wherein the optimized operation sequence logic pauses operation when one of the following conditions occurs: (a) point loss; (b) oxygen detected; (c) low steam pressure; (d) modifier flow deviation from desired flow; (e) back pressure alarm while a reactor point is being taken in service; and (f) activation of interlocks.

9. The method of claim 1, wherein the method comprises a process of switching an operation from conditions optimized for producing a first product to conditions optimized for producing a second product, the process comprising at least steps (IV), (V), and (VI), and the optimized operation sequence logic in step (IV) of the switching starts from a beginning of a production of the final batch of the first product to an end of the production of a first batch of the second product.

10. The method of claim 9, wherein the optimized operation sequence logic in the process of switching comprises adjusting one or more of initiator, reactor pressure, reactor temperature, modifier material, modifier flow, and jacket water systems (JWS) temperature control.

11. The method of claim 9, wherein at least one of the following applies:
(a) the first product is an ethylene-vinyl acetate copolymer; and the second product is an ethylene homopolymer;
(b) the first product is an ethylene homopolymer, and the second product is an ethylene-vinyl acetate copolymer;
(c) the first product is a high-density polyolefin, and the second product is a medium-density polyolefin; and
(d) the first product is a medium-density polyolefin, and the second product is a high-density polyolefin.

12. The method of claim 8, wherein the optimized operation sequence logic pauses normal operation when one of the following conditions occurs: (a) point loss; (b) back pressure alarm; (c) rod loading constraints on high pressure compressor; and (d) modifier flow deviation from desired flow.

13. The method of claim 8, wherein the optimized operation sequence logic in a grade transition uses a means for a procedural operations sequence.

14. The method of claim 1, wherein the method comprises a process of defouling a reactor starting from when average conversion from a beginning of the previous defouling cycle exceeds real-time conversion, the process comprising at least steps (IV), (V), and (VI).

15. The method of claim 14, wherein optimized operation sequence logic in step (IV) of the process of defouling the reactor comprises: (a) from the jacket water systems (JWS) at the beginning of the reactor to that at the end of the reactor, increasing jacket water systems temperatures to a defouling target temperature; (b) keeping all temperatures at their respective defouling target for a period of time; and (c) decreasing the temperatures to a recipe value, from the beginning to the end of the reactor, Inherent components of elements recited have antecedent basis in the recitation of the components themselves, For example, the limitation "the outer surface of said sphere" would not require an antecedent recitation that the sphere has an outer surface, See Bose Corp. v. JBL, Inc., 274 F.3d 1354, 1359, 61 USPQ2d 1216, 1218-19 (Fed. Cir 2001) (holding that recitation of "an ellipse" provided antecedent basis for "an ellipse having a major diameter" because "[t]here can be no dispute that mathematically an inherent characteristic of an ellipse is a major diameter").

16. The method of claim 15, wherein the defouling target temperature is between about 180° C. and about 200° C.

17. The method of claim 15, wherein the period of time is determined by calculating defouling degree based on a correlation of JWS temperatures to light-off temperatures.

18. The method of claim 17, wherein the correlation is a linear correlation until defouling starts.

19. The method of claim 18, wherein reactor defouling is stopped upon a moment when deviation from the linear correlation stops increasing.

20. The method of claim 15, wherein the recipe value in step (c) is below 90° C.

21. The method of claim 1, the method comprising a process of defouling A recycle implementing at least steps (IV), (V), and (VI), wherein:
the process comprises automatically increasing and decreasing temperatures of coolers for each train, and changing modifier control and reactor peak temperature.

22. The method of claim 1, wherein the method comprises a process of packing a modifier for a reactor implementing at least steps (IV), (V), and (VI), wherein:
the process comprises automatically injecting an amount of modifier after a start-up.

23. The method of claim 22, wherein step (IV) includes determining the amount of modifier according to (a) required concentration of the modifier for a particular grade; and (b) total amount of the modifier and vinyl acetate (VA) remaining in the unit.

24. The method of claim 1, wherein the current operation comprises at least one of reactor start-up, grade transition, reactor defouling, recycle defouling, and modifier packing for start-up.

\* \* \* \* \*